United States Patent
Tachibana

(10) Patent No.: US 12,217,852 B2
(45) Date of Patent: Feb. 4, 2025

(54) IMAGE PROCESSING DEVICE, IMAGE PROCESSING METHOD, IMAGE PROCESSING PROGRAM, LEARNING DEVICE, LEARNING METHOD, LEARNING PROGRAM, AND DERIVATION MODEL

(71) Applicant: FUJIFILM Corporation, Tokyo (JP)

(72) Inventor: Atsushi Tachibana, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 383 days.

(21) Appl. No.: 17/699,190

(22) Filed: Mar. 21, 2022

(65) Prior Publication Data

US 2022/0215936 A1 Jul. 7, 2022

Related U.S. Application Data

(63) Continuation of application No. PCT/JP2020/036255, filed on Sep. 25, 2020.

(30) Foreign Application Priority Data

Sep. 27, 2019 (JP) .................. 2019-177220

(51) Int. Cl.
- *G16H 30/40* (2018.01)
- *G06F 17/12* (2006.01)
- *G06T 7/00* (2017.01)

(52) U.S. Cl.
CPC ............. *G16H 30/40* (2018.01); *G06F 17/12* (2013.01); *G06T 7/0012* (2013.01); *G06T 2207/10081* (2013.01); *G06T 2207/30088* (2013.01)

(58) Field of Classification Search
CPC ....... G16H 30/40; G06F 17/12; G06T 7/0012; G06T 2207/10081; G06T 2207/30088;
(Continued)

(56) References Cited

U.S. PATENT DOCUMENTS

| | | |
|---|---|---|
| 2014/0002076 A1 | 1/2014 | Warntjes |
| 2015/0177350 A1 | 6/2015 | Warntjes |

(Continued)

FOREIGN PATENT DOCUMENTS

| | | |
|---|---|---|
| JP | 2015525604 | 9/2015 |
| JP | 2017086337 | 5/2017 |

(Continued)

OTHER PUBLICATIONS

Qing Lyu et al., Quantitave MRI- absolute T1, T2 and proton density parameters from deep learning (Year: 2018).*

(Continued)

*Primary Examiner* — Dhaval V Patel
(74) *Attorney, Agent, or Firm* — JCIPRNET

(57) ABSTRACT

An image acquisition unit acquires at least one target medical image having a representation format different from an MRI image. A tissue eigenvalue derivation unit has a derivation model constructed by machine learning using a plurality of teacher data to, in a case in which at least one medical image having the representation format different from the MRI image is input, output a tissue eigenvalue of MRI for the input medical image, and inputs the target medical image to the derivation model to derive the tissue eigenvalue for the target medical image.

14 Claims, 4 Drawing Sheets

(58) Field of Classification Search
CPC ............. G06T 2211/441; G06T 11/001; G06T 11/008; G06N 3/045; A61B 5/055
See application file for complete search history.

(56) References Cited

U.S. PATENT DOCUMENTS

| | | | |
|---|---|---|---|
| 2017/0131373 A1 | 5/2017 | Takeshima et al. | |
| 2017/0372497 A1* | 12/2017 | Hu | ............... G06T 5/90 |
| 2018/0336677 A1 | 11/2018 | Sloan et al. | |
| 2018/0374246 A1 | 12/2018 | Igarashi et al. | |
| 2019/0282192 A1* | 9/2019 | Goshen | ............... G06T 7/155 |
| 2019/0362522 A1* | 11/2019 | Han | ............... A61B 5/055 |
| 2021/0225491 A1* | 7/2021 | Jin | ............... A61B 5/055 |
| 2021/0257094 A1* | 8/2021 | Takemoto | ............ A61B 6/5247 |
| 2021/0295108 A1* | 9/2021 | Bar | ............... G06V 10/764 |

FOREIGN PATENT DOCUMENTS

| | | |
|---|---|---|
| JP | 2018505705 | 3/2018 |
| JP | 2018192264 | 12/2018 |
| JP | 2018198682 | 12/2018 |
| JP | 2019005557 | 1/2019 |
| WO | 2019098780 | 5/2019 |

OTHER PUBLICATIONS

"Office Action of Japan Counterpart Application" with English translation thereof, issued on Jun. 6, 2023, p. 1-p. 6.

"Office Action of Japan Counterpart Application" with English translation thereof, issued on Apr. 4, 2023, p. 1-p. 5.

Cheng-Bin Jin et al., "Deep CT to MR Synthesis Using Paired and Unpaired Data," Sensors 2019, May 2019, pp. 1-19.

J.B.M. Warntjes et al., "Rapid Magnetic Resonance Quantification on the Brain: Optimization for Clinical Usage," Magnetic Resonance in Medicine, Aug. 2008, pp. 320-329.

Yicheng Chen et al., "MR-based PET Attenuation Correction for Brain PET-MR Using Support Vector Machines," Proc. Intl. Soc. Mag. Reson. Med. 23, 2015, pp. 1-1.

Andrew Palmera Leynes et al., "Direct Pseudo-CT Image Synthesis Using Deep Learning for Pelvis PET/MR Attenuation Correction," Proc. Intl. Soc. Mag. Reson. Med. 25, 2017, pp. 1-4.

"International Search Report (Form PCT/ISA/210) of PCT/JP2020/036255," mailed on Nov. 24, 2020, with English translation thereof, pp. 1-5.

"Written Opinion of the International Searching Authority (Form PCT/ISA/237)" of PCT/JP2020/036255, mailed on Nov. 24, 2020, with English translation thereof, pp. 1-6.

"Search Report of Europe Counterpart Application", issued on Oct. 24, 2022, p. 1-p. 6.

"Notice of Reasons for Refusal of Japan Counterpart Application", issued on Oct. 18, 2022, with English translation thereof, p. 1-p. 6.

Can Zhao et al., "Whole Brain Segmentation and Labeling from CT Using Synthetic MR Images," Conference: International Workshop on Machine Learning in Medical Imaging, Sep. 2017, pp. 291-298.

Philippe Meyer et al., "Survey on deep learning for radiotherapy," Comput Biol Med., vol. 98, May 2018, pp. 126-146.

Kiaohuan Cao et al., "Dual-core Steered Non-rigid Registration for Multi-modal Images via Bi-directional Image Synthesis," Medical Image Analysis, vol. 41, May 2017, pp. 18-31.

* cited by examiner

IMAGE PROCESSING DEVICE, IMAGE PROCESSING METHOD, IMAGE PROCESSING PROGRAM, LEARNING DEVICE, LEARNING METHOD, LEARNING PROGRAM, AND DERIVATION MODEL

CROSS REFERENCE TO RELATED APPLICATIONS

The present application is a Continuation of PCT International Application No. PCT/JP2020/036255, filed on Sep. 25, 2020, which claims priority to Japanese Patent Application No. 2019-177220, filed on Sep. 27, 2019. Each application above is hereby expressly incorporated by reference, in its entirety, into the present application.

BACKGROUND

Technical Field

The present disclosure relates to an image processing device, an image processing method, an image processing program, a learning device, a learning method, a learning program, and a derivation model.

Related Art

In recent years, with the progress of medical apparatuses, such as a computed tomography (CT) apparatus and a magnetic resonance imaging (MRI) apparatus, a three-dimensional image having a higher quality and a higher resolution has been used for image diagnosis. As described above, the acquired three-dimensional image has a different representation format depending on the apparatus, that is, the modality. For example, even in a case in which the tissue is the same, the density may be different or the contrast of the entire image may be different in the representation format. Therefore, a lesion, which is not visible in the three-dimensional image acquired by one modality, may be visible in the three-dimensional image acquired by another modality. Therefore, the accuracy of diagnosis can be improved by acquiring the three-dimensional images having different representation formats depending on a plurality of types of modality.

On the other hand, a method of converting a CT image into an MRI image by using a conversion model constructed by machine learning has been proposed (see Deep CT to MR Synthesis Using Paired and Unpaired Data, Sensors 2019. 19(10), 2361 below). The method described in Deep CT to MR Synthesis Using Paired and Unpaired Data, Sensors 2019. 19(10), 2361 is a method in which the conversion model is constructed by machine learning using the CT image and a T2-weighted image of MRI as teacher data, and the CT image is converted into the T2-weighted image of MRI by using the constructed conversion model. By using the method described in Deep CT to MR Synthesis Using Paired and Unpaired Data, Sensors 2019. 19(10), 2361, it is possible to acquire the MRI image only by performing imaging with the CT apparatus without performing imaging with both the CT apparatus and the MRI apparatus.

In addition, there is known technology of generating any type of computing image computationally after imaging by using the MRI image acquired by the MRI apparatus and a predetermined parameter. For example, in JP2019-005557A, JP2015-525604A, and Rapid magnetic resonance quantification on the brain: Optimization for clinical usage, Magn Reson Med 2008. 60(2), 320-329, a method of deriving a tissue eigenvalue, such as a T1 value, a T2 value, and proton density (PD), by simulation and curve fitting using a theoretical formula of a signal value of the MRI image by using the MRI image acquired while changing imaging conditions has been proposed. It is possible to derive the MRI image having any representation format, such as a T1-weighted image, the T2-weighted image, and a diffusion-weighted image, by calculating the tissue eigenvalue derived by using the method described in JP2019-005557A, JP2015-525604A, and Rapid magnetic resonance quantification on the brain: Optimization for clinical usage, Magn Reson Med 2008. 60(2), 320-329 with an arithmetic expression using various parameters. Therefore, it is not necessary to perform imaging a plurality of times to acquire the MRI images having different representation formats, so that the burden on a patient, and a medical cost can be reduced.

In the method described in JP2019-005557A, JP2015-525604A, and Rapid magnetic resonance quantification on the brain: Optimization for clinical usage, Magn Reson Med 2008. 60(2), 320-329, it is necessary to perform imaging by the MRI apparatus to derive the tissue eigenvalue. However, imaging with the MRI apparatus is contraindicated in a patient with an implantable pacemaker and a patient with claustrophobia. Therefore, for such a patient, it is not possible to acquire the MRI image or derive any type of the MRI image by acquiring the tissue eigenvalue. On the other hand, by using the method described in Deep CT to MR Synthesis Using Paired and Unpaired Data, Sensors 2019. 19(10), 2361, it is possible to convert the CT image into the MRI image. However, the conversion model generated by learning can only derive the MRI image having a single representation format. Therefore, in order to derive the MRI images having a plurality of representation formats from the CT image, it is necessary to construct the conversion model for each representation format of the MRI image, so that a load for constructing the conversion model is large.

SUMMARY

The present disclosure has been made in view of the above circumstances, and is to enable easy acquisition of an MRI image having a desired representation format.

An image processing device according to the present disclosure comprises an image acquisition unit that acquires at least one target medical image having a representation format different from an MRI image, and a tissue eigenvalue derivation unit that has a derivation model constructed by machine learning using a plurality of teacher data to, in a case in which at least one medical image having the representation format different from the MRI image is input, output a tissue eigenvalue of MRI for the input medical image, and inputs the target medical image to the derivation model to derive the tissue eigenvalue for the target medical image.

Note that the image processing device according to the present disclosure, the target medical image and the medical image may be CT images.

In addition, in the image processing device according to the present disclosure, the target medical image and the medical image may be a plurality of CT images for the same subject, which are acquired by using radiation having different energy distributions, respectively.

Here, the plurality of CT images having different energy distributions, which are acquired by imaging the subject by using radiation having different energy distributions, can be acquired by, for example, a dual energy CT apparatus or a photon counting CT apparatus.

In addition, in the image processing device according to the present disclosure, the derivation model may be constructed by performing machine learning using the plurality of teacher data including a medical image for learning including a specific structure of a subject, and a tissue eigenvalue for learning for the same subject as the subject.

In addition, in the image processing device according to the present disclosure, the tissue eigenvalue may be a T1 value, a T2 value, and a proton density (PD) value.

In addition, the image processing device according to the present disclosure may further comprise an MRI image derivation unit that derives a predetermined type of MRI image by using the tissue eigenvalue.

In addition, the image processing device according to the present disclosure may further comprise a display control unit that displays the MRI image on a display unit.

In addition, in the image processing device according to the present disclosure, the display control unit may further display the target medical image on the display unit.

A learning device according to the present disclosure comprises a learning unit that constructs a derivation model by performing machine learning using a plurality of teacher data to, in a case in which at least one medical image having a representation format different from an MRI image is input, output a tissue eigenvalue of MRI for the medical image.

Note that, in the learning device according to the present disclosure, the teacher data may include a medical image for learning including a specific structure of a subject, and a tissue eigenvalue for learning for the same subject as the subject, and the learning unit may perform the machine learning by inputting the medical image for learning to the derivation model, outputting the tissue eigenvalue from the derivation model, and using a difference between the output tissue eigenvalue and the tissue eigenvalue for learning as a loss.

A derivation model according to the present disclosure, which is constructed by performing machine learning using a plurality of teacher data to, in a case in which at least one medical image having a representation format different from an MRI image is input, output a tissue eigenvalue of MRI for the medical image.

An image processing method according to the present disclosure comprises acquiring at least one target medical image having a representation format different from an MRI image, and providing a derivation model constructed by machine learning using a plurality of teacher data to, in a case in which at least one medical image having the representation format different from the MRI image is input, output a tissue eigenvalue of MRI for the input medical image, and inputting the target medical image to the derivation model to derive the tissue eigenvalue for the target medical image.

A learning method according to the present disclosure comprises constructing a derivation model by performing machine learning using a plurality of teacher data to, in a case in which at least one medical image having a representation format different from an MRI image is input, output a tissue eigenvalue of MRI for the medical image.

Note that the image processing method and the learning method according to the present disclosure may be provided as programs to be executed by a computer.

Another image processing device according to the present disclosure comprises a memory that stores an instruction to be executed by a computer, and a processor configured to execute the stored instruction, in which the processor executes processing of acquiring at least one target medical image having a representation format different from an MRI image, and providing a derivation model constructed by machine learning using a plurality of teacher data to, in a case in which at least one medical image having the representation format different from the MRI image is input, output a tissue eigenvalue of MRI for the input medical image, and inputting the target medical image to the derivation model to derive the tissue eigenvalue for the target medical image.

Another learning device according to the present disclosure comprises a memory that stores an instruction to be executed by a computer, and a processor configured to execute the stored instruction, in which the processor executes processing of constructing a derivation model by performing machine learning using a plurality of teacher data to, in a case in which at least one medical image having a representation format different from an MRI image is input, output a tissue eigenvalue of MRI for the medical image.

According to the present disclosure, even in a case in which a patient is contraindicated for MRI, a plurality of types of MRI images of the patient can be easily obtained without using a plurality of conversion models.

DETAILED DESCRIPTION

Figure 1:
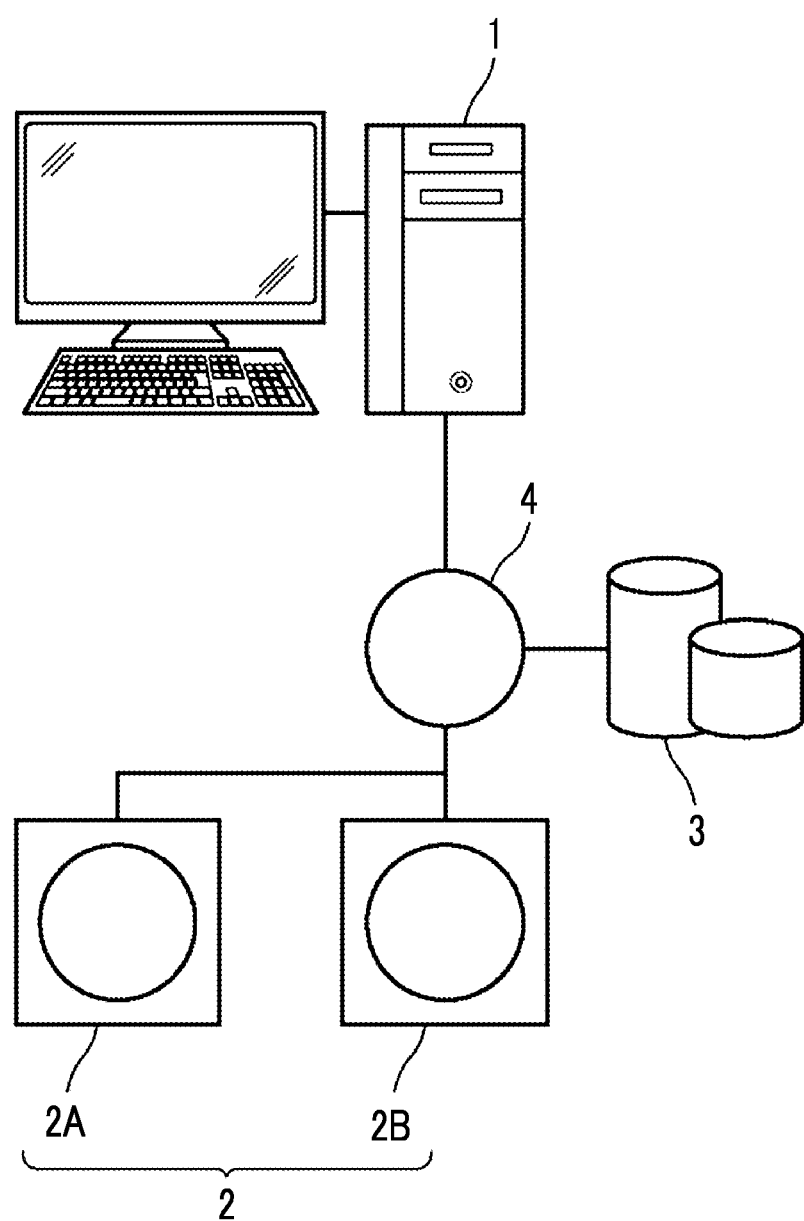
FIG. 1 is a hardware configuration diagram showing an outline of a diagnosis support system to which an image processing device according to an embodiment of the present disclosure is applied.

In the following, an embodiment of the present disclosure will be described with reference to the drawings. FIG. 1 is a hardware configuration diagram showing an outline of a diagnosis support system to which an image processing device according to the embodiment of the present disclosure is applied. As shown in FIG. 1, in the diagnosis support system, an image processing device 1 according to the present embodiment, a modality 2, and an image storage server 3 are connected in a communicable state via a network 4.

The modality 2 is an apparatus that images a diagnosis target site of a subject to generate a three-dimensional image showing the diagnosis target site, and specifically, is a CT apparatus, an MRI apparatus, a positron emission tomography (PET) apparatus, and the like. The three-dimensional image including of a plurality of slice images generated by the modality 2 is transmitted to and stored in the image storage server 3. Note that in the present embodiment, it is assumed that the modality 2 includes a CT apparatus 2A and an MRI apparatus 2B. In addition, it is assumed that the CT apparatus 2A is a dual energy CT apparatus or a photon counting CT apparatus capable of imaging a subject by using radiation having different energy distributions. It is assumed that the MRI apparatus 2B can derive a tissue eigenvalue of MRI by imaging the subject, which is described in JP2015-

525604A and Rapid magnetic resonance quantification on the brain: Optimization for clinical usage, Magn Reson Med 2008. 60(2), 320-329, for example.

The image storage server 3 is a computer that stores and manages various data, and comprises a large capacity external storage device and software for database management. The image storage server 3 performs communication with other devices via the wired or wireless network 4 to transmit and receive image data and the like. Specifically, the image storage server 3 acquires various data including the image data of a medical image generated by the modality 2 via the network, and stores and manages the image data in a recording medium, such as the large capacity external storage device. Note that a storage format of the image data and the communication between the devices via the network 4 are based on a protocol, such as digital imaging and communication in medicine (DICOM). In addition, in the present embodiment, the image storage server 3 also stores and manages a plurality of teacher data to be described below.

The image processing device 1 according to the present embodiment is a computer in which an image processing program and a learning program according to the present embodiment is installed. The computer may be a workstation or a personal computer directly operated by a doctor who makes a diagnosis, or a server computer connected to the workstation or the personal computer via the network. Alternatively, the image processing program and the learning program are stored in a storage device of the server computer connected to the network or a network storage in a state of being accessible from the outside, and are downloaded and installed in the computer used by the doctor in response to a request. Alternatively, the image processing program and the learning program are distributed in a state of being recorded on a recording medium, such as a digital versatile disc (DVD) or a compact disc read only memory (CD-ROM), and are installed in the computer from the recording medium.

Figure 2:
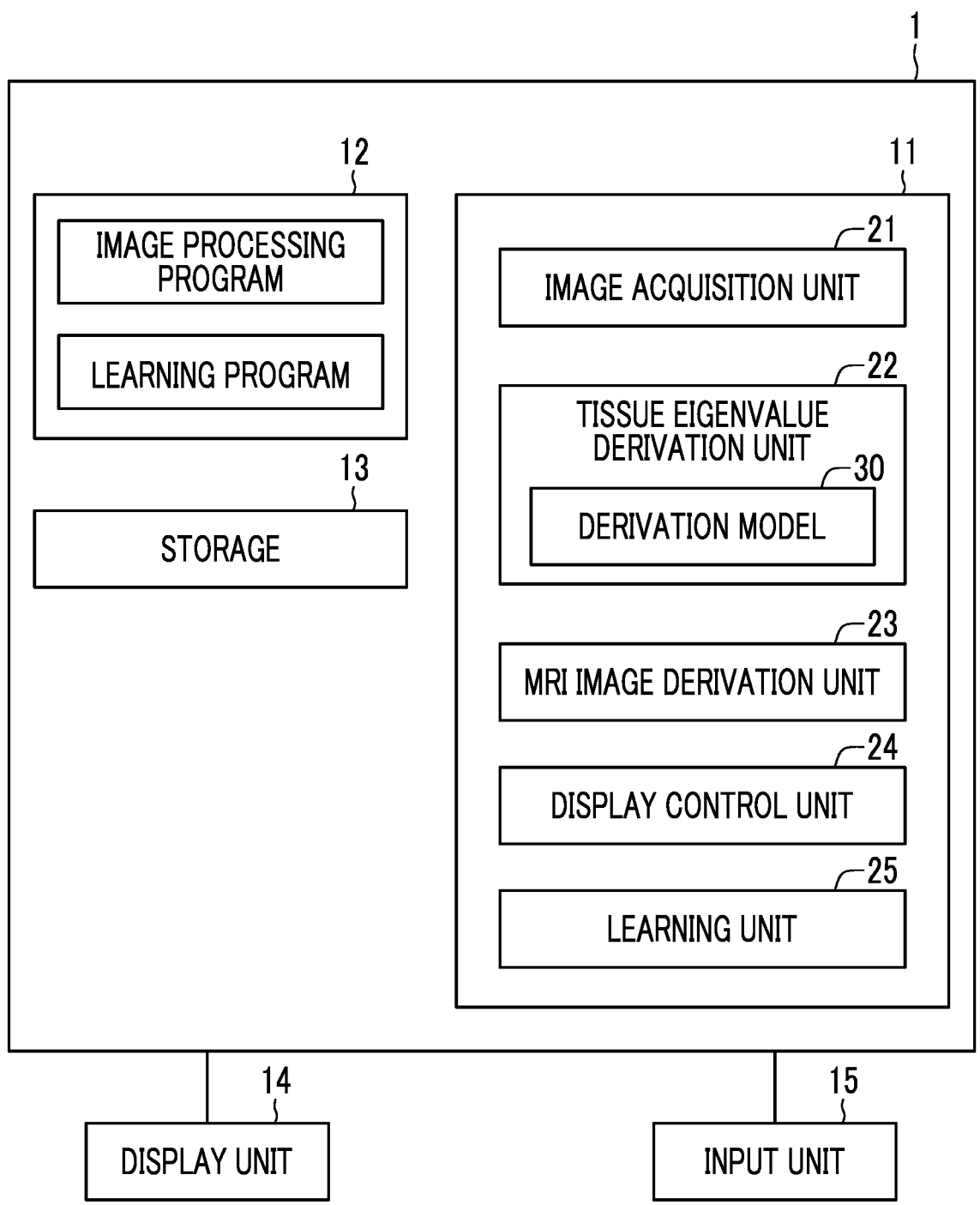
FIG. 2 is a schematic block diagram showing a configuration of the image processing device according to the present embodiment.

FIG. 2 is a diagram showing a schematic configuration of the image processing device realized by installing the image processing program and the learning program in the computer. As shown in FIG. 2, the image processing device 1 comprises a central processing unit (CPU) 11, a memory 12, and a storage 13, as a configuration of a standard workstation. In addition, the image processing device 1 is connected with a display unit 14, such as a liquid crystal display, and an input unit 15, such as a keyboard or a mouse.

The storage 13 is configured by a hard disk drive or the like, and stores the CT images, which is a processing target, a plurality of teacher data, and various pieces of information including information necessary for processing, which are acquired from the image storage server 3 via the network 4.

In addition, the image processing program and the learning program are stored in the memory 12. The image processing program defines, as processing to be executed by the CPU 11, image acquisition processing of acquiring a target medical image having the representation format different from the MRI image, tissue eigenvalue derivation processing of deriving the tissue eigenvalue of MRI for the target medical image, MRI image derivation processing of deriving the MRI image of a desired representation format by using the tissue eigenvalue, display control processing of displaying the derived MRI image on the display unit 14. The learning program defines, as processing to be executed by the CPU 11, learning processing of constructing a derivation model by performing machine learning using the plurality of teacher data to, in a case in which at least one medical image having the representation format different from the MRI image is input, output the tissue eigenvalue of MRI for the medical image.

Moreover, the CPU 11 executes the processing according to the image processing program and the learning program, so that the computer functions as an image acquisition unit 21, a tissue eigenvalue derivation unit 22, an MRI image derivation unit 23, a display control unit 24, and a learning unit 25.

The image acquisition unit 21 acquires the target medical image having the representation format different from the MRI image from the image storage server 3 via an interface (not shown) connected to the network. In addition, the plurality of teacher data used for learning are acquired from the image storage server 3. Note that in the present embodiment, the target medical image is the CT image acquired by the CT apparatus 2A. In addition, in the present embodiment, the CT apparatus 2A is the dual energy CT apparatus or the photon counting CT apparatus capable of imaging the subject by using radiation having different energy distribution. Therefore, in the present embodiment, it is assumed that one or more CT images Ci (i=1 to n) acquired by imaging the same site of the same subject are used as the target medical image.

The tissue eigenvalue derivation unit 22 has a derivation model 30 constructed by machine learning to, in a case in which the CT image is input, output the tissue eigenvalue of MRI for the input CT image. Moreover, the tissue eigenvalue derivation unit 22 derives the tissue eigenvalue by inputting the target CT image Ci into the derivation model 30 and outputting the tissue eigenvalue of MRI for the CT image Ci from the derivation model 30. In the present embodiment, it is assumed that a T1 value, a T2 value, and a PD value are derived as the tissue eigenvalues.

In the following, machine learning for constructing the derivation model 30 will be described. The learning unit 25 performs machine learning for constructing the derivation model 30. The learning unit 25 constructs the derivation model 30 by performing machine learning using the teacher data including a combination of a CT image for learning and a tissue eigenvalue for learning. In the present embodiment, it is assumed that the derivation model 30 is constructed by machine learning a convolutional neural network (hereinafter, referred to as CNN), which is one of a multi neural network in which a plurality of processing layers are hierarchically connected and deep learning is performed.

The CNN includes a plurality of convolutional layers and pooling layers. The convolutional layer performs convolution processing using various kernels on the input image, and outputs a feature amount map including feature amount data obtained by the convolution processing. The kernel has an n×n pixel size (for example, n=3), and a weight is set for each element. Specifically, the weight, such as a differential filter that emphasizes the edge of the input image, are set. The convolutional layer applies the kernel to the entire input image or the feature amount map output from the processing layer in the previous stage while shifting an attention pixel of the kernel. Further, the convolutional layer applies an activation function, such as a sigmoid function, to a convolved value, and outputs the feature amount map.

The pooling layer reduces an amount of data in the feature amount map by pooling the feature amount map output by the convolutional layer, and outputs the feature amount map with the reduced amount of data.

Moreover, by repeating the outputting and pooling of the feature amount map in each processing layer, the tissue eigenvalue for each pixel of the input CT image is output from the final layer of the CNN.

Figure 3:
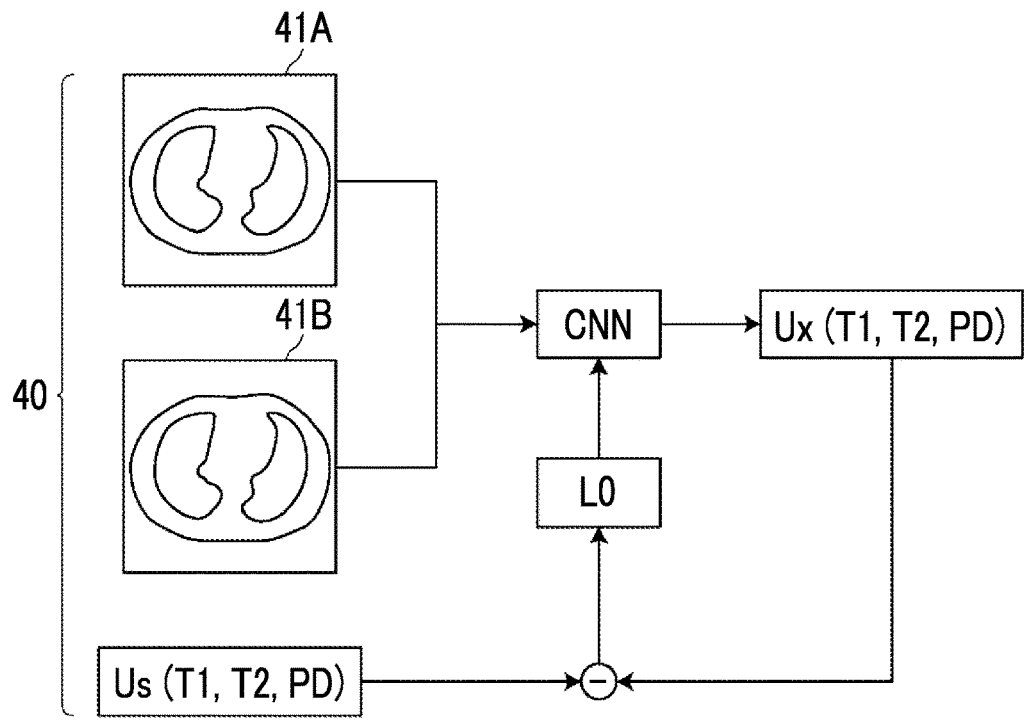
FIG. 3 is a conceptual diagram of machine learning performed in the present embodiment.

FIG. 3 is a conceptual diagram of machine learning performed in the present embodiment. Note that although machine learning using two CT images will be described here, one CT image may be used or three or more CT images may be used.

First, the teacher data will be described. In the present embodiment, teacher data 40 includes a combination of CT images for learning 41A and 41B having different energy distributions, which are acquired by irradiating the subject with the radiation having different energy distributions in the CT apparatus 2A, and the tissue eigenvalue for learning (that is, the T1 value, T2 value, and the PD value) Us acquired by imaging the same subject as the subject for which the CT images for learning 41A and 41B in the MRI apparatus 2B and acquired by using the method described in JP2019-005557A, JP2015-525604A, and Rapid magnetic resonance quantification on the brain: Optimization for clinical usage, Magn Reson Med 2008. 60(2), 320-329.

As shown in FIG. 3, the learning unit 25 inputs the CT images for learning 41A and 41B included in the teacher data to the CNN, and outputs a tissue eigenvalue Ux for the CT images for learning 41A and 41B from the CNN. The learning unit 25 derives a loss L0 based on a difference between the output tissue eigenvalue Ux and the tissue eigenvalue for learning Us. The loss L0 is the difference between the T1 value, T2 value, and PD value of the output tissue eigenvalue Ux and the T1 value, T2 value, and PD value of the tissue eigenvalue for learning Us.

Moreover, the learning unit 25 learns the CNN by using a large number of teacher data such that the loss L0 is equal to or less than a predetermined threshold value. Specifically, learning of the CNN is performed by deriving the number of convolutional layers and the number of pooling layers, which configure the CNN, and a coefficient of the kernel and magnitude of the kernel in the convolutional layer, such that the loss L0 is equal to or less than the predetermined threshold value. As a result, in a case in which the CT image Ci is input to the trained CNN, the CNN outputs the tissue eigenvalue for each pixel of the CT image Ci. Note that the learning unit 25 may perform learning a predetermined number of times instead of learning such that the loss L0 is equal to or less than the predetermined threshold value.

As described above, the learning unit 25 performs machine learning of the CNN, so that the derivation model 30 that outputs the tissue eigenvalue for each pixel of the CT image Ci in a case in which the CT image Ci is input is constructed.

Returning to FIG. 2, the MRI image derivation unit 23 derives the MRI image by using the tissue eigenvalue derived by the tissue eigenvalue derivation unit 22. Here, the MRI image has various representation formats, such as a T1-weighted image, a T2-weighted image, a fat suppression image, and a diffusion-weighted image, and the contrast, that is, the appearance differs depending on the representation format. For example, on the T1-weighted image, mostly, a fat tissue appears white, water, a humoral component, and a cyst appear black, and a tumor appears slightly black. In addition, on the T2-weighted image, water, a humoral component, and a cyst appear white, as well as the fat tissue.

These various representation formats of the MRI images can be derived by calculating the tissue eigenvalues, that is, the T1 value, the T2 value, and the PD value, by using a predetermined parameter. Specifically, the MRI image having a desired representation format can be generated by calculating the T1 value, the T2 value, and the PD value by using a predetermined arithmetic expression to which parameters, such as an inversion time TI, an echo time TE, and a repetition time TR, depending on the representation format are applied.

Here, in the present embodiment, a table and an arithmetic expression defining a relationship between the representation formats of various MRI images and various parameters are stored in the storage 13. The MRI image derivation unit 23 reads out the parameters corresponding to the representation format of the MRI image previously input from the input unit 15 from the storage 13. Moreover, an MRI image MO having the input representation format is derived by calculating the T1 value, the T2 value, and the PD value by using the read out parameters.

Figure 4:
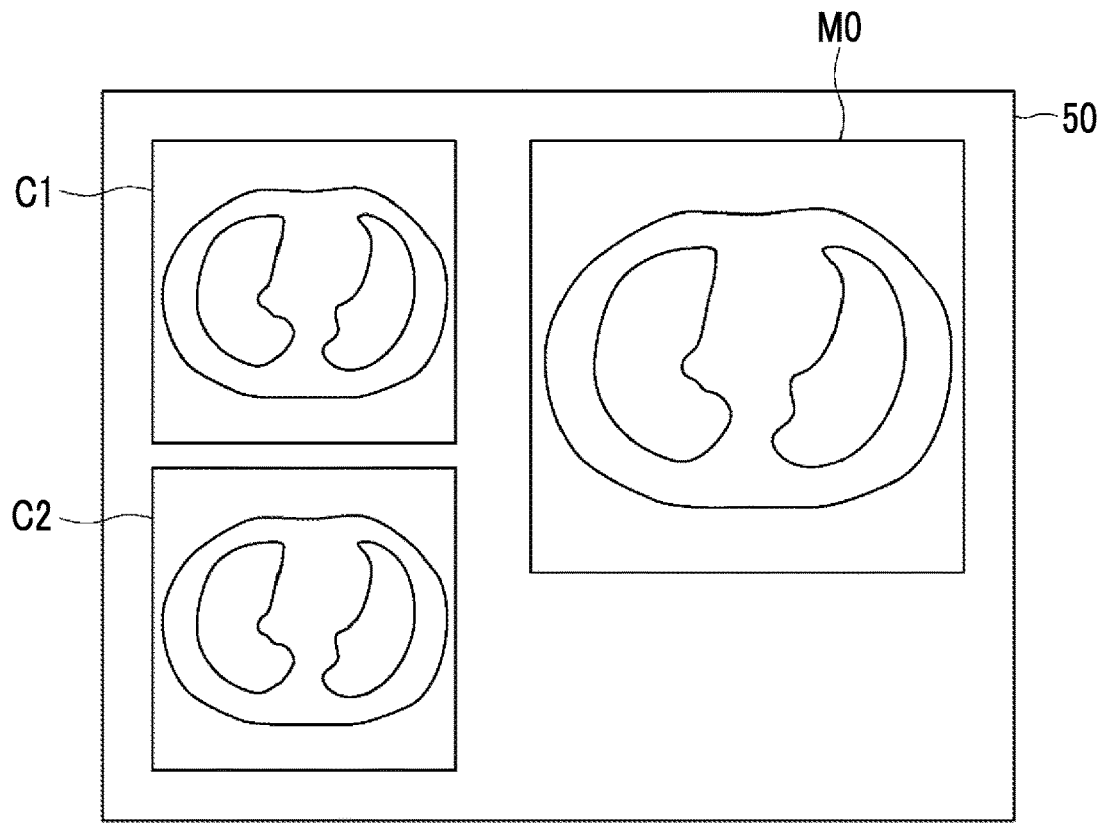
FIG. 4 is a diagram showing a display screen of an MRI image.

The display control unit 24 displays the MRI image MO derived by the MRI image derivation unit 23 on the display unit 14. FIG. 4 is a diagram showing a display screen of the MRI image. As shown in FIG. 4, on a display screen 50, two CT images C1 and C2 used for generating the MRI image MO are also displayed together with the MRI image MO. As a result, it is possible to perform image interpretation with the feature of the representation format of each image by using two types of CT images C1 and C2, and the MRI image MO for the same patient.

Figure 5:
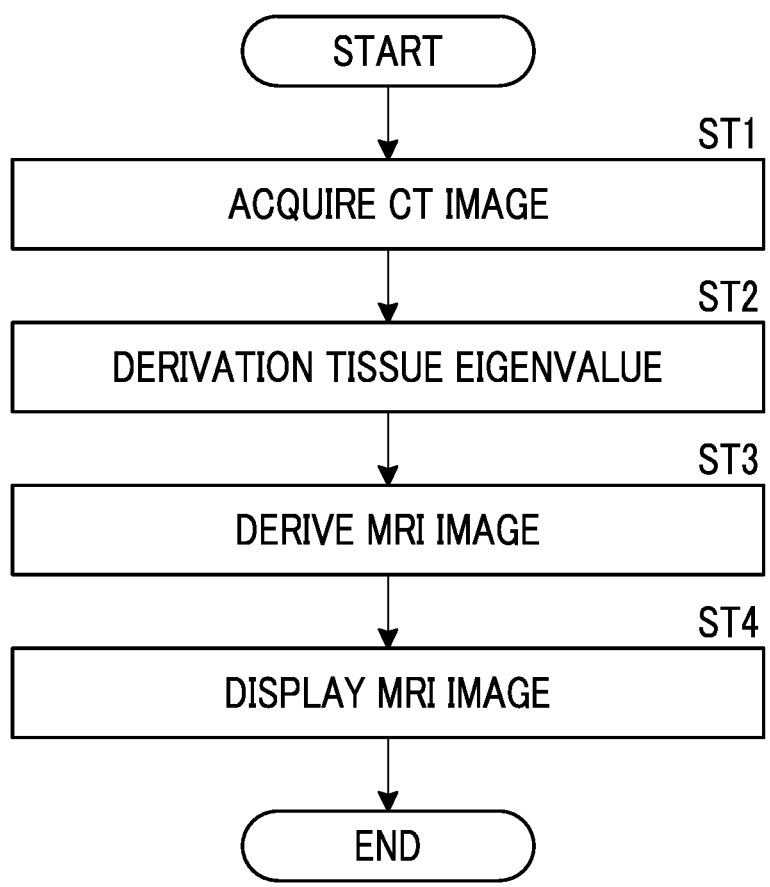
FIG. 5 is a flowchart showing processing performed in the present embodiment.

Then, processing performed in the present embodiment will be described. FIG. 5 is a flowchart showing the processing performed in the present embodiment. Note that it is assumed that the CT image Ci, which is the processing target, is acquired from the image storage server 3 and stored in the storage 13. In a case in which a processing start instruction is input from the input unit 15, the image acquisition unit 21 acquires the CT image Ci, which is the processing target, from the storage 13 (step ST1). Then, the tissue eigenvalue derivation unit 22 derives the tissue eigenvalue of MRI for the CT image Ci by the derivation model 30 (step ST2). Moreover, the MRI image derivation unit 23 derives the MRI image MO having a desired representation format by using the tissue eigenvalue (step ST3). Further, the display control unit 24 displays the MRI image MO on the display unit 14 (step ST4), and terminates the processing.

As described above, in the present embodiment, the tissue eigenvalue of MRI for the CT image Ci is derived by inputting the CT image Ci having the representation format different from the MRI image. Here, by using the tissue eigenvalue, it is possible to generate the MRI image having any representation format. Therefore, even in a case in which the patient has contraindications to MRI, such as having a pacemaker implanted or having claustrophobia, it is possible to acquire the MRI image having a desired representation format for the patient. In addition, it is not necessary to prepare a conversion model for converting the image corresponding to each of the representation formats of the MRI image. Therefore, according to the present embodiment, it is possible to easily acquire the MRI image having a desired representation format for the patient.

Here, since a maintenance cost of the MRI apparatus is high, it is difficult to introduce the MRI apparatus in a small hospital, such as a private hospital. On the other hand, a maintenance cost of the CT apparatus is not so high, it can be easily introduced in a small hospital, such as a private hospital. In addition, a medical cost for the CT image are cheaper than the MRI image. Therefore, by using the CT image as the medical image, which is the processing target, it is possible to acquire the MRI image by using the image that can be acquired relatively easily and cheaply.

In addition, by using a plurality of the CT images having different representation formats, an amount of information for deriving the tissue eigenvalue can be increased, so that the tissue eigenvalue of MRI can be derived more accurately.

Note that in the embodiment described above, the tissue eigenvalue of MRI is derived from the CT image Ci, but the present disclosure is not limited to this. The tissue eigenvalue of MRI may be derived from other medical image (e.g. PET image) other than the CT image Ci. In this case, the derivation model 30 need only be constructed by performing learning of the CNN by using a combination of the medical image for learning of the other medical image (i.e. PET image), and the tissue eigenvalue for learning for the same subject as the subject for which the image is acquired, as the teacher data.

In addition, in the embodiment described above, the CNN is used as the derivation model 30, but the present disclosure is not limited to this. In addition to the CNN, a support vector machine (SVM), a deep neural network (DNN), a recurrent neural network (RNN), and the like can be used.

In addition, in the embodiment described above, the image processing device 1 is assumed to include the learning unit 25, but the present disclosure is not limited to this. The derivation model 30 may be constructed by a learning device separate from the image processing device 1, and the constructed derivation model 30 may be applied to the tissue eigenvalue derivation unit 22 of the image processing device 1.

In addition, in the embodiment described above, the image processing device 1 includes the MRI image derivation unit 23 and the display control unit 24, but the present disclosure is not limited to this. The MRI image may be derived or the derived MRI image may be displayed by the MRI image derivation unit 23 provided in a device different from the image processing device 1. In this case, the tissue eigenvalue derived by the image processing device 1 is stored in an external device, such as the image storage server 3, is read out from the external device as needed, and is used for deriving the MRI image or the like.

In addition, in the embodiment described above, for example, various processors shown below can be used as the hardware structures of processing units that execute various pieces of processing, such as the image acquisition unit 21, the tissue eigenvalue derivation unit 22, the MRI image derivation unit 23, the display control unit 24, and the learning unit 25. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. As described above, as the hardware structure, various processing units are configured by one or more of various processors described above.

Moreover, as the hardware structures of these various processors, more specifically, it is possible to use an electric circuit (circuitry) in which circuit elements such as semiconductor elements are combined.

What is claimed is:

1. An image processing device comprising at least one processor, wherein the processor is configured to:
   acquire at least one target medical image having a representation format different from an MRI image; and
   input the target medical image to a derivation model to derive the tissue eigenvalue for the target medical image, wherein the derivation model being constructed by machine learning using a plurality of teacher data to, in a case in which at least one medical image having the representation format different from the MRI image is input, output a plurality of tissue eigenvalues of MRI for the input medical image, wherein the plurality of tissue eigenvalues represents different representation formats of MRI; and
   generate a derived MRI image based on the tissue eigenvalue of MRI derived by the derivation model through the target medical image having the representation format different from the MRI image.

2. The image processing device according to claim 1, wherein the target medical image and the medical image are CT images.

3. The image processing device according to claim 1, wherein the target medical image and the medical image are a plurality of CT images for the same subject, which are acquired by using radiation having different energy distributions, respectively.

4. The image processing device according to claim 1, wherein the derivation model is constructed by performing machine learning using the plurality of teacher data including a medical image for learning including a specific structure of a subject, and a tissue eigenvalue for learning for the same subject as the subject.

5. The image processing device according to claim 1, wherein the tissue eigenvalue is a T1 value, a T2 value, and a proton density (PD) value.

6. The image processing device according to claim 1, wherein the processor is further configured to derive a predetermined type of MRI image by using the tissue eigenvalue.

7. The image processing device according to claim 6, wherein the processor is further configured to display the MRI image on a display.

8. The image processing device according to claim 7, wherein the processor is configured to display the target medical image on the display.

9. A learning device comprising: at least one processor, wherein the processor is configured to construct a derivation model by performing machine learning using a plurality of teacher data to, in a case in which at least one medical image having a representation format different from an MRI image is input, output a plurality of tissue eigenvalues of MRI for the medical image, wherein the plurality of tissue eigenvalues represent different representation formats of MRI.

10. The learning device according to claim 9,
wherein the teacher data includes a medical image for learning including a specific structure of a subject, and a tissue eigenvalue for learning for the same subject as the subject, and the processor is configured to perform the machine learning by inputting the medical image for learning to the derivation model, outputting the tissue eigenvalue from the derivation model, and using a difference between the output tissue eigenvalue and the tissue eigenvalue for learning as a loss.

11. An image processing method comprising:
acquiring at least one target medical image having a representation format different from an MRI image; and inputting the target medical image to a derivation model to derive the tissue eigenvalue for the target medical image, wherein the derivation model being constructed by machine learning using a plurality of teacher data to, in a case in which at least one medical image having the representation format different from the MRI image is input, output a plurality of tissue eigenvalues of MRI for the input medical image, wherein the plurality of tissue eigenvalues represents different representation formats of MRI; and generating a derived MRI image based on the tissue eigenvalue of MRI derived by the derivation model through the target medical image having the representation format different from the MRI image.

12. A learning method comprising:
constructing a derivation model by performing machine learning using a plurality of teacher data to, in a case in which at least one medical image having a representation format different from an MRI image is input, output a plurality of tissue eigenvalues of MRI for the medical image, wherein the plurality of tissue eigenvalues represent different representation formats of MRI.

13. A non-transitory computer-readable storage medium that stores an image processing program causing a computer to execute:

a procedure of acquiring at least one target medical image having a representation format different from an MRI image; and a procedure of inputting the target medical image to a derivation model to derive the tissue eigenvalue for the target medical image, wherein the derivation model being constructed by machine learning using a plurality of teacher data to, in a case in which at least one medical image having the representation format different from the MRI image is input, output plurality of tissue eigenvalues of MRI for the input medical image, wherein the plurality of tissue eigenvalues represents different representation formats of MRI; and a procedure of generating a derived MRI image based on the tissue eigenvalue of MRI derived by the derivation model through the target medical image having the representation format different from the MRI image.

14. A non-transitory computer-readable storage medium that stores a learning program causing a computer to execute:

a procedure of constructing a derivation model by performing machine learning using a plurality of teacher data to, in a case in which at least one medical image having a representation format different from an MRI image is input, output a plurality of tissue eigenvalues of MRI for the medical image, wherein the plurality of tissue eigenvalues represent different representation formats of MRI.

* * * * *